US00PP29532P3

(12) United States Plant Patent
Devereux

(10) Patent No.: US PP29,532 P3
(45) Date of Patent: Jul. 17, 2018

(54) ***RUDBECKIA* PLANT NAMED 'RRISU01-0'**

(50) Latin Name: *Rudbeckia hirta*
Varietal Denomination: RRISU01-0

(71) Applicant: James Devereux, Fort Collins, CO (US)

(72) Inventor: James Devereux, Fort Collins, CO (US)

( * ) Notice: Subject to any disclaimer, the term of this patent is extended or adjusted under 35 U.S.C. 154(b) by 0 days.

(21) Appl. No.: 15/330,570

(22) Filed: Oct. 13, 2016

(65) Prior Publication Data

US 2018/0110174 P1 Apr. 19, 2018

(51) Int. Cl.
*A01H 5/02* (2018.01)

(52) U.S. Cl.
USPC ..... Plt./474
CPC ..... *A01H 5/025* (2013.01)

(58) Field of Classification Search
USPC ..... Plt./474
CPC ..... A01H 5/025; A01H 5/02; A01H 5/00
See application file for complete search history.

(56) References Cited

PUBLICATIONS

University of New Hampshire Cooperative Extension 2015 *Rudbeckia hirta* Black Eyed Susan, retrieved on Sep. 26, 2017, retrieved from the Internet at https://extension.unh.edu/resources/files/Resource002434_Rep3640.pdf one page. (Year: 2015).*

* cited by examiner

*Primary Examiner* — June Hwu
(74) *Attorney, Agent, or Firm* — Cassandra Bright

(57) ABSTRACT

A new and distinct *Rudbeckia hirta* cultivar named 'RRISU01-0' is disclosed, characterized by early season flowering. Plants exhibit exceptional cold hardiness for the species and can be successfully propagated by conventional vegetative cuttings. The new variety is an *Rudbeckia*, and is normally used as a garden or container plant.

2 Drawing Sheets

Figure 1:
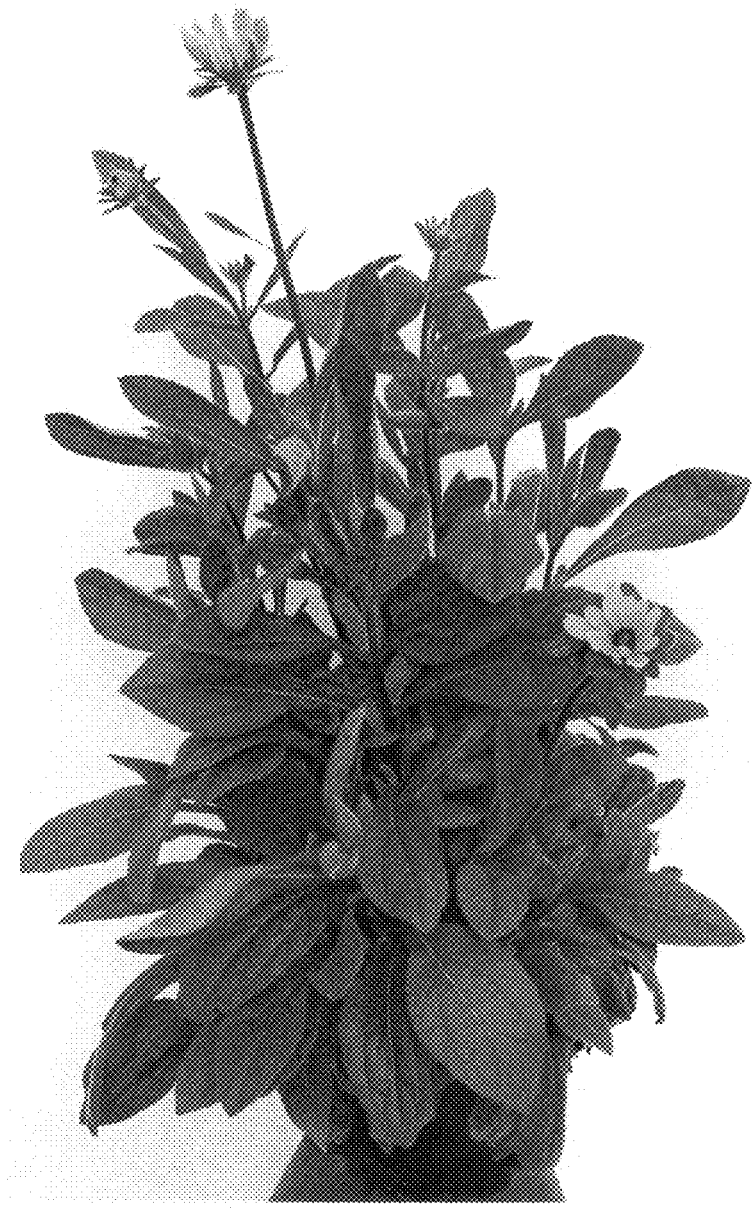

Latin name of the genus and species: *Rudbeckia hirta.*
Variety denomination: 'RRISU01-0'.

BACKGROUND OF THE INVENTION

The new cultivar was discovered as a chance, whole plant mutation in a personal backyard in Fort Collins, Colo. The inventor discovered the new variety as a naturally occurring whole plant mutation among several plants of unnamed, unpatented, *Rudbeckia hirta*. The new variety was discovered in July of 2012 by the inventor.

Asexual reproduction of the new cultivar 'RRISU01-0' by terminal vegetative cuttings was performed at a commercial nursery in Santa Paula, Calif. October 2013. Subsequently, reproduction has also been successful by tissue culture. Vegetative reproduction by meristem tissue culture has produced several generations, and has shown that the unique features of this cultivar are stable and reproduced true to type through successive generations.

SUMMARY OF THE INVENTION

The cultivar 'RRISU01-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RRISU01-0.' These characteristics in combination distinguish 'RRISU01-0' as a new and distinct *Rudbeckia hirta* cultivar:

1. *Rudbeckia hirta* are annuals in garden conditions. RRISU01-0 is longer lived and has been maintained for over 5 years in trial conditions.
2. *Rudbeckia hirta* cannot survive temperatures below freezing for extended periods of time. RRISU01-0 has overwintered in trial locations in Colorado where annual *Rudbeckia hirta* will not survive. Trials have taken place over 5 years.
3. While *Rudbeckia hirta* requires long July days (14 hours is cited in seed company's catalogs and websites) to initiate flowers, RRISU01-0 will initiate flowers as early as February or 10.5 hour days.
4. *Rudbeckia hirta* will produce flowers for approximately 4 months per year (July to September), while RRISU01-0 will flower from May (April or earlier in warmer locations) to October (November in warmer locations).
5. *Rudbeckia hirta* is propagated from seeds or tissue culture, while RRISU01-0 has been successfully propagated by vegetative terminal cuttings for 5 trial production cycles (years).

PARENT COMPARISON

Plants of the new cultivar 'RRISU01-0' are similar to plants of the parent variety in most horticultural characteristics. However, plants of the new cultivar 'RRISU01-0 have been observed to tolerate cold better than the parent variety. Additionally, the new variety has been observed to begin flowering approximately 2 months earlier.

COMMERCIAL COMPARISON

In addition to the parent variety, 'RRISU01-0' can also be compared to the unpatented, commercially known variety

*Rudbeckia hirta* 'Denver Daisy', unpatented. The new variety can be produced by vegetative cuttings, whereas 'Denver Daisy' cannot. The new variety has been observed to tolerate temperatures than 'Denver Daisy' and begins flowering approximately 2 months earlier.

'RRISU01-0' can also be compared to the unpatented, commercially known variety *Rudbeckia hirta* 'Prairie Sun', unpatented. The new variety can be produced by vegetative cuttings, whereas 'Prairie Sun', cannot. The new variety has been observed to tolerate lower temperatures than 'Prairie Sun', and begins flowering approximately 2 months earlier.

BRIEF DESCRIPTION OF THE PHOTOGRAPHS

The accompanying photograph in FIG. 1 illustrates in full color a typical plant and flowers of 'RRISU01-0' grown in a greenhouse in Santa Paula, Calif. The plant is approximately 14 weeks old.

Figure 2:
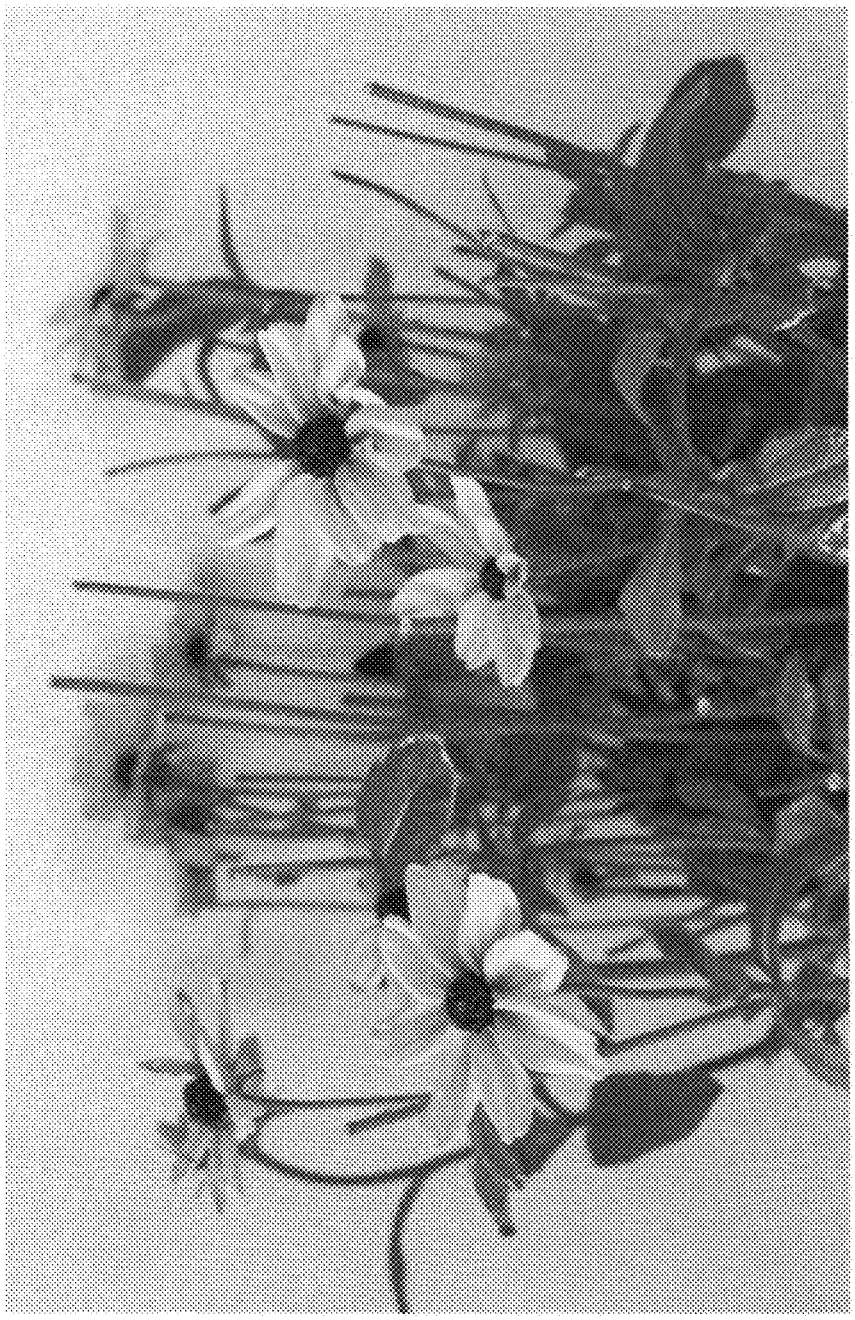

FIG. 2 illustrates a more mature plant of approximately 7 months.

The photographs were taken using conventional techniques and although colors may appear different from actual colors due to light reflectance it is as accurate as possible by conventional photographic techniques.

DETAILED BOTANICAL DESCRIPTION

In The following description, color references are made to The Royal Horticultural Society Colour Chart 2007, except where general terms of ordinary dictionary significance are used. The following observations and measurements describe 'RRISU01-0' plants grown in a greenhouse in Santa Paula, Calif. Summer growing temperature ranged from approximately 14 to 33° C. during the day and 6 to 18° C. at night. Measurements and numerical values represent averages of typical flowering types. No chemical or photoperiodic treatments were given.

Botanical classification: *Rudbeckia hirta* 'RRISU01-0.'.

PROPAGATION

Time to initiate rooting: 7 to 10 days at approximately 25° C.

Time to produce a young rooted liner: Approximately 40 days at approximately 22° C.

Root description: Fine, well-branched, fibrous, becoming slightly woody with age.

PLANT

Growth habit: Hardy, upright, herbaceous perennial.

Height:

*To top of foliar plane*.—Approximately 33 cm.

*To top of flowering plane*.—Approximately 38 cm.

Plant spread: Approximately 53 cm.

Growth rate: Moderate. Approximately 15 cm per months during Spring months, while actively growing.

Branching characteristics: Basal and low lateral branching. Well branched.

Length of branches: Approximately 22 to 26 cm, excluding inflorescence.

Diameter branches: Approximately 6 to 8 mm.

Quantity of branches: Approximately 7 basal branches, each basal branch with 3 to 5 lateral branches.

Texture of lateral branches: Hispid. Hairs 1 to 3 mm long, colored near White 155A.

Color of lateral branches: Between RHS Yellow-Green 144A and Green 143A. Younger branches with thin stripes of Greyed-Purple 187A.

Aspect: Approximately 15' angle from base of plant.

Strength of lateral branches: Very strong.

Internode length: Average range 3.0 to 7.2 cm.

Age of plant described: Approximately 5 to 6 months old.

FOLIAGE

Leaf:

*Arrangement*.—Flowering stems produce opposite occurring foliage. Basal foliage occurs in irregular whorls. Mature, non-flowering stems produce alternate occurring foliage.

*Average length*.—Average range 14.2 to 21.0 cm.

*Average width*.—Average range 4.6 to 6.5 cm.

*Shape of blade*.—Narrow spatulate.

*Apex*.—Acute.

*Base*.—Attenuate.

*Attachment*.—Sessile.

*Margin*.—Sparsely serrate.

*Texture of top surface*.—Rough with a matte appearance. Moderately covered with hispid hairs. Average hair length approximately 2 mm, colored near RHS White 155A.

*Texture of bottom surface*.—Rough with a matte appearance. Moderately covered with hispid hairs. Average hair length approximately 2 mm, colored near RHS White 155A.

*Leaf internode length*.—Approximately 4 to 6 cm.

*Color*.—Young foliage upper side: Near RHS Green 137A, but darker. Young foliage under side: Near RHS Green 137C. Mature foliage upper side: Near RHS Green 137A, but darker. Mature foliage under side: Near RHS Green 137B.

*Venation*.—Type: Pinnate. Venation color upper side: Near RHS Yellow-Green 144C. Venation color under side: Near RHS Green 138A.

FLOWER

Bloom period: Naturally blooming continuously from Summer to mid-Fall. During this time, blooming begins approximately 20 weeks after planting a rooted liner.

Bud:

*Bud shape*.—Globular.

*Bud length*.—Approximately 8 mm.

*Bud diameter*.—Approximately 9 mm.

*Bud color*.—Near Green 143A. Center near Greyed-Purple N186B.

Inflorescence:

*Form*.—Terminal capitulum consisting of numerous disc florets, one or two rows of ray florets and two rows of involucral bracts.

Flower:

*Diameter of entire flower*.—Average range 6.0 to 7.5 cm.

*Depth of flower*.—Approximately 2.0 cm.

*Disc diameter*.—Approximately 1.4 cm.

*Receptacle shape*.—Conical.

*Receptacle height*.—Average 1.0 cm.

*Receptacle diameter*.—Average 5 mm.

*Receptacle color*.—Near RHS White N155B.

*Quantity of inflorescences per lateral stem*.—1.

*Quantity of open inflorescence and buds per plant.*—Average 10 to 30.
*Longevity.*—Average 2 weeks on the plant without significant fading or aging. Persistent.
*Fragrance.*—No fragrance.

Ray florets:
*Arrangement.*—Rotate.
*Shape.*—Elliptic, or double elliptic.
*Number of ray florets.*—Average range 8 to 15.
*Length.*—Approximately 3.5 cm.
*Width.*—Approximately 1.5 to 1.8 cm.
*Apex shape.*—Round, or 2 double lobes, with round apices.
*Base.*—Attenuate.
*Margin.*—Entire.
*Texture all surfaces.*—Smooth, matte, slightly ribbed lengthwise.

Color:
Ray florets:
*Upper surface at first opening.*—Upper section near Yellow-Orange 17C, base near 17A.
*Upper surface at maturity.*—Upper section near Yellow-Orange 17C, base near 17A.
*Upper surface at fading.*—Upper section near Yellow-Orange 17C, base near 17A. Faint streaks appear in upper half, near Green 143C.
*Under surface at first opening.*—Near RHS Yellow 12B, veins near Green 143A.
*Under surface at maturity.*—Near RHS Yellow 12B, veins near Green 143B, faint flushing near 143C between veins.
*Under surface at fading.*—Near RHS Yellow 12B, veins near Green 143B, flushing near 143C between veins.

Disc florets:
*Number of disc florets.*—Approximately 150.
*Arrangement.*—Acropetally on disc.
*Length.*—Approximately 5 to 7 mm.
*Width.*—Approximately 1 mm.
*Shape.*—Tubular.
*Margin.*—Entire.
*Apex.*—Rounded.
*Base.*—Fused.
*Texture.*—Smooth, glossy.

Color disc florets:
*At first opening.*—Near RHS Greyed-Purple N186C, base near White 155A.
*At maturity.*—Near RHS Greyed-Purple N186A, base near White 155A.
*Fading.*—Near RHS Greyed-Purple N186A.

Phyllaries/involucal bracts:
*Arrangement.*—Rotate, in 2 rows.
*Number.*—Approximately 15 to 20.
*Length.*—Average range 8 to 11 mm.
*Width.*—Approximately 0.3 mm.
*Shape.*—Lanceolate.
*Apex.*—Acute.
*Base.*—Broadly cuneate.
*Margin.*—Entire.
*Texture.*—Pubescent, with long hairs occurring along margin.
*Color.*—Inside color near RHS Green N137A. Outside color near RHS Green 137B.

PEDUNCLE

*Length.*—Average range 15 to 30 cm.
*Width.*—Average 5 mm.
*Texture.*—Hispid.
*Color.*—Near RHS Green 143A.
*Strength.*—Very strong.

REPRODUCTIVE ORGANS

Ray florets: No floral parts observed in ray florets to date.
Disc florets:
Androecium:
*Stamen number.*—3 or 4.
*Filament length.*—Average 3 mm.
*Filament color.*—Lower section near White 155C, upper section near Greyed-Purple N186A.
*Anther shape.*—Oblong.
*Anther length.*—0.5 mm.
*Anther color.*—Greyed-Purple N186A.
*Pollen amount.*—Moderate.
*Pollen color.*—Near Yellow-Orange 15A.

Gynoecium:
*Pistil length.*—Approximately 4 mm.
*Stigma shape.*—Decurrent.
*Stigma color.*—Near RHS Greyed-Purple N187A.
*Style length.*—About 3 mm.
*Style color.*—Lower section near White 155C, upper section near Greyed-Purple N186A.
*Ovary color.*—Near RHS White 155C.

OTHER CHARACTERISTICS

Disease resistance: Neither resistance nor susceptibility to diseases or pests normal to *Rudbeckia* have been observed in this variety.

Drought tolerance and temperature tolerance: Hardy perennial, low temperature tolerance to USDA Zone 4, at least. Tolerates high temperature extremely well, to at least 35° C. Some drought tolerance. Plants can be allowed in dry soil for several days without damage.

Seed: Low seed production. Oblong achene, approximately 3 mm long, 1 mm wide, colored near RHS Brown 200A.

What is claimed is:

1. A new and distinct cultivar of *Rudbeckia* plant named 'RRISU01-0' as herein illustrated and described.

* * * * *